United States Patent [19]  [11] 4,008,080
Wagner  [45] Feb. 15, 1977

[54] COPPER FREE DENTAL GOLD ALLOYS

[75] Inventor: Ewald Wagner, Pforzheim, Germany

[73] Assignee: Deutsche Gold- und Silber-Scheideanstalt vormals Roessler, Frankfurt, Germany

[22] Filed: Nov. 4, 1975

[21] Appl. No.: 628,766

[30] Foreign Application Priority Data

Nov. 13, 1974 Germany .......................... 2453799

[52] U.S. Cl. ................................ 75/134 N; 75/165; 75/173 R
[51] Int. Cl.$^2$ .......................................... C22C 5/02
[58] Field of Search ............ 75/165, 134 N, 172 G, 75/173 R

[56] References Cited

UNITED STATES PATENTS

| | | | |
|---|---|---|---|
| 3,667,936 | 6/1972 | Katz | 75/134 N |
| 3,767,391 | 10/1973 | Tuccillo et al. | 75/165 X |
| 3,819,366 | 6/1974 | Katz | 75/165 X |

FOREIGN PATENTS OR APPLICATIONS

| | | | |
|---|---|---|---|
| 2,139,331 | 2/1973 | Germany | 75/165 |
| 683,004 | 11/1952 | United Kingdom | 75/165 |

Primary Examiner—L. Dewayne Rutledge
Assistant Examiner—E. L. Weise
Attorney, Agent, or Firm—Cushman, Darby & Cushman

[57] ABSTRACT

There is provided a copper free dental gold alloy that contains 25 to 40% silver, 40 to 60% gold, 5 to 20% palladium, 0.05 to 0.5% iridium, 0 to 6% indium, 0 to 6% tin and 0 to 2% zinc with the proviso that at least 2% of the named non-noble metals are present, all percents are weight percents.

9 Claims, No Drawings

COPPER FREE DENTAL GOLD ALLOYS

The invention is directed to a copper free dental gold alloy based on silver-gold-palladium containing a relatively low gold content.

For dental purposes, for example for the production of crowns and bridges, there have been used gold alloys for a long period of time. Such alloys originally were formed only of gold, silver and copper. Beginning at about the start of the 20th century there were developed alloys in which a part of the gold was first replaced by platinum and later also by other metals of the platinum group, especially palladium. Alloys of this type with various physical properties are listed for example in the "Specification No. 7 for Dental Casting Gold Alloy" of the Federation Dentaire Internationale; in which the sum of the content of gold and metals of the platinum group in the individual types should amount to at least 75, 78 or 83 weight percent in order to guarantee their resistance to corrosion.

Then for economical reasons a few years ago there were developed relatively cheap materials based on silver-gold-palladium which contained 20 to 35% silver, 50 to 60% gold and 5 to 10% palladium. The remainder of 0 to 15% consisted mostly of copper and zinc. Since the total content of gold and palladium amounted to at least about 50 atomic percent these alloys had a sufficient resistance to corrosion. To be sure this concentration limit of 50 atomic percent which is designated by Tammann as the resistance limit is not very sharply pronounced in solid solution-alloys of gold with several components. However, it also depends on the type of electrolytes acting on them. It has, therefore, been found favorable to so select the content of gold plus platinum metals that it is over 50 atomic percent, normally even over 55 atomic percent.

It is known that dental alloys can be discolored in the mouth if local elements are formed which are traced back to differential aeration. In a casting whose surfaces show shrinkage porosities, for example differential aeration cells can form. The surfaces of the alloy which are wetted by saliva and air, thereby become cathodes while in the depth of the cavities anodic areas arise, since there the available oxygen is less. The alloy components which are less noble than oxygen, as for example copper, can be dissolved there as ions. They wander to the cathodic region and then are deposited. Frequently, the thin precipitate is scarcely seen. Under the action of food and air it can change into plainly visible oxide and/or sulfide films. Also in telescopic work, the danger of coloration is present, since the primary part is always more poorly aerated than the secondary crown. The deciding role in this discoloration must be reduced to the copper of the alloy.

Wagner, German Offenlegungsschrift 2,139,331 discloses copper free dental gold alloys which contain 65 to 85% gold, 4 to 20% silver, 2 to 10% platinum, 1 to 4% indium, 2 to 10% palladium, 0.5 to 2% zinc, 0.05 to 5% iridium and 0.5 to 2% tin. In this kind of alloy, coloration by oral fluids do not occur and because of their high noble metal content they are very resistant to corrosion. Their higher noble metal content, however, makes it expensive especially their gold and platinum content.

Therefore, it was the problem of the present invention to find a copper free dental gold alloy which despite reduced noble metal content are corrosion resistant and fulfills the mechanical properties of the FDI specification (FDI = Federation Dentaire Internationale).

This problem was solved by using alloys which consisted of 25 to 40% silver, 40 to 60% gold, 5 to 20% palladium, 0.05 to 0.5% iridium, 0 to 6% indium, 0 to 6% tin and 0 to 2% zinc with the proviso that the normal non-noble metals must total at least 2%.

Especially favorable properties were found with alloys that consisted of 28 to 35% silver, 50 to 58% gold, 5 to 10% palladium, 0.05 to 0.15% iridium, 2 to 5% indium, 0 to 3% tin and 0 to 1% zinc wherein the non-noble metal content is at least 4%.

The dental alloys of the invention contain significantly less gold than the previously known copper free dental gold alloys and the expensive platinum is eliminated without the mechanical and chemical corrosion resistant properties falling out of the FDI specifications.

In the following table there are set forth a series of alloy compositions according to the invention with increasing concentrations of palladium. The hardness values in the table show that with increasing palladium content the hardness increases both in the soft (or mild) annealed condition and in the fully hardened state.

The sum of the content of gold, palladium and iridium expressed in atomic percent is slightly over 50%, except in alloys 2, 3, 4 and 13 in which the sum is below 50%. Despite this relatively low content of gold, palladium and iridium, the alloys are corrosion resistant.

Based on their mechanical properties, the alloys are arranged in the FDI Specification No. 7 as Type I (soft), II (medium), III (hard) and IV (extra hard). Especially approved are alloys 3 (Type I), 5 and 6 (Type II), 7 and 10 (Type III), 13 and 14 (Type IV).

Unless otherwise indicated, all parts and percentages are by weight.

The compositions can consist essentially of or consists of the stated materials.

TABLE

| Alloy | Ag | Au | Composition in % In | Ir | Pd | Sn | Zn | Vickers Quenched | number Hardened (Maximum) | Melting Range °C | Au+Pd+Ir Atomic-% |
|---|---|---|---|---|---|---|---|---|---|---|---|
| 1 | 30.0 | 60.0 | 2.5 | 0.1 | 4.9 | 2.5 | — | 103 | 161 | 1020 – 850 | 52.2 |
| 2 | 35.0 | 55.0 | 2.5 | 0.1 | 4.9 | 2.5 | — | 103 | 161 | 1015 – 855 | 47.0 |
| 3 | 35.0 | 55.0 | 5.0 | 0.1 | 4.9 | — | — | 70 | 143 | 1030 – 940 | 47.0 |
| 4 | 35.0 | 55.0 | — | 0.1 | 4.9 | 5.0 | — | 96 | 143 | 1010 – 820 | 47.0 |
| 5 | 30.0 | 58.0 | 3.0 | 0.1 | 6.4 | 2.0 | 0.5 | 110 | 183 | 1020 – 860 | 51.9 |
| 6 | 29.5 | 58.0 | 3.0 | 0.1 | 6.4 | 2.0 | 1.0 | 114 | 183 | 1010 – 860 | 51.7 |
| 7 | 30.5 | 55.0 | 3.0 | 0.1 | 8.4 | 2.0 | 1.0 | 118 | 220 | 1035 – 870 | 51.2 |
| 8 | 30.5 | 55.0 | 5.0 | 0.1 | 8.4 | — | 1.0 | 137 | 210 | 1030 – 940 | 51.2 |
| 9 | 30.0 | 55.0 | 5.0 | 0.1 | 9.9 | — | — | 143 | 218 | 1095 – 1015 | 53.6 |
| 10 | 30.0 | 55.0 | 2.5 | 0.1 | 9.9 | 2.5 | — | 127 | 192 | 1070 – 930 | 53.6 |
| 11 | 30.0 | 55.0 | — | 0.1 | 9.9 | 5.0 | — | 107 | 143 | 1070 – 940 | 53.8 |

TABLE-continued

| Alloy | Ag | Au | Composition in % | | | Sn | Zn | Vickers Quenched | number Hardened (Maximum) | Melting Range °C | Au+Pd+Ir Atomic-% |
| | | | In | Ir | Pd | | | | | | |
| --- | --- | --- | --- | --- | --- | --- | --- | --- | --- | --- | --- |
| 12 | 35.0 | 50.0 | 2.5 | 0.1 | 9.9 | 2.5 | — | 118 | 175 | 1070 – 940 | 48.2 |
| 13 | 29.0 | 55.0 | 4.0 | 0.1 | 9.9 | 1.0 | 1.0 | 143 | 232 | 1065 – 940 | 53.2 |
| 14 | 28.0 | 55.0 | 5.0 | 0.1 | 9.9 | 1.0 | 1.0 | 148 | 236 | 1040 – 915 | 53.2 |
| 15 | 35.0 | 45.0 | 2.5 | 0.1 | 14.9 | 2.5 | — | 143 | 175 | 1120 – 990 | 50.1 |

What is claimed is:

1. A copper free dental gold alloy consisting essentially of 25 to 40% silver, 40 to 60% gold, 5 to 20% palladium, 0.05 to 0.5% iridium, 0 to 6% indium 0 to 6% tin and 0 to 2% zinc, with the proviso that the named non-noble metals are present in a total amount of at least 2%.

2. The alloy of claim 1 consisting essentially of 28 to 35% silver, 50 to 58% gold, 5 to 10% palladium, 0.05 to 0.15% iridium, 2 to 5% indium, 0 to 3% tin and 0 to 1% zinc, with the proviso that the named non-noble metals are present in a total amount of at least 4%.

3. The alloy of claim 1 consisting essentially of 35.0% Ag, 55.0% Au, 5.0% In, 0.1% Ir, and 4.9% Pd.

4. The alloy of claim 1 consisting essentially of 30.0% Ag, 58.0% Au, 3.0% In, 0.1% Ir, 6.4% Pd, 2.0% Sn and 0.5% Zn.

5. The alloy of claim 1 consisting essentially of 29.5% Ag, 58.0% Au, 3.0% In, 0.1% Ir, 6.4% Pd, 2.0% Sn and 1.0% Zn.

6. The alloy of claim 1 consisting essentially of 30.5% Ag, 55.0% Au, 3.0% In, 0.1% Ir, 8.4% Pd, 2.0% Sn and 1.0% Zn.

7. The alloy of claim 1 consisting essentially of 30.0% Ag, 55% Au, 2.5% In, 0.1% Ir, 9.9% Pd and 2.5% Sn.

8. The alloy of claim 1 consisting essentially of 29.0% Ag, 55.0% Au, 4.0% In, 0.1% Ir, 9.9% Pd, 1.0% Sn and 1.0% Zn.

9. The alloy of claim 1 consisting essentially of 28.0% Ag, 55.0% Au, 5.0% In, 0.1% Ir, 9.9% Pd, 1.0% Sn and 1.0% Zn.

* * * * *